United States Patent [19]

Hain et al.

[11] Patent Number: 4,513,891
[45] Date of Patent: Apr. 30, 1985

[54] SPRAY DISPENSING CONTAINER AND VALVE THEREFOR

[75] Inventors: Robert W. Hain, Scotch Plains; Frederick B. Hadtke, New Providence, both of N.J.; Myron Paikoff, Colonie, N.Y.

[73] Assignee: Sterling Drug Inc., New York, N.Y.

[21] Appl. No.: 368,722

[22] Filed: Apr. 15, 1982

[51] Int. Cl.³ .............................................. B05B 11/04
[52] U.S. Cl. .................................... 222/213; 222/494; 604/213
[58] Field of Search ............... 222/206, 211, 213, 478, 222/481, 490, 491, 494, 215; 604/204, 212, 213, 214, 215, 216

[56] References Cited

U.S. PATENT DOCUMENTS

| | | | |
|---|---|---|---|
| 1,977,227 | 10/1934 | Berendt | 222/494 X |
| 2,115,959 | 5/1938 | Lewis | 604/212 |
| 2,752,199 | 6/1956 | Newell, Jr. | 222/211 |
| 3,199,787 | 8/1965 | Oishei et al. | 222/490 |
| 3,221,945 | 12/1965 | Davis, Jr. | 222/211 |

*Primary Examiner*—Joseph J. Rolla
*Assistant Examiner*—Kevin P. Shaver
*Attorney, Agent, or Firm*—William G. Webb; B. Woodrow Wyatt; Paul E. Dupont

[57] ABSTRACT

A spray dispenser of the squeeze bottle type, for use in the administration of nasal sprays, comprises a squeeze bottle in combination with a spray dispenser head assembly consisting of a cap, and associated spray nozzle which functions as a two-way check valve and a dip tube for conveying liquid from the bottle to the spray nozzle. The head may optionally be fitted with an overcap for protecting the spray head from contamination when not in use.

21 Claims, 6 Drawing Figures

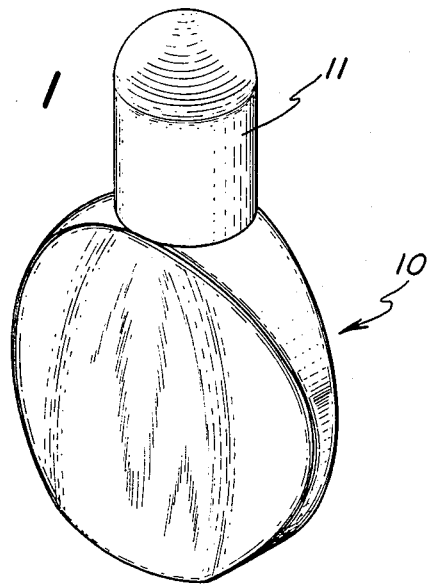
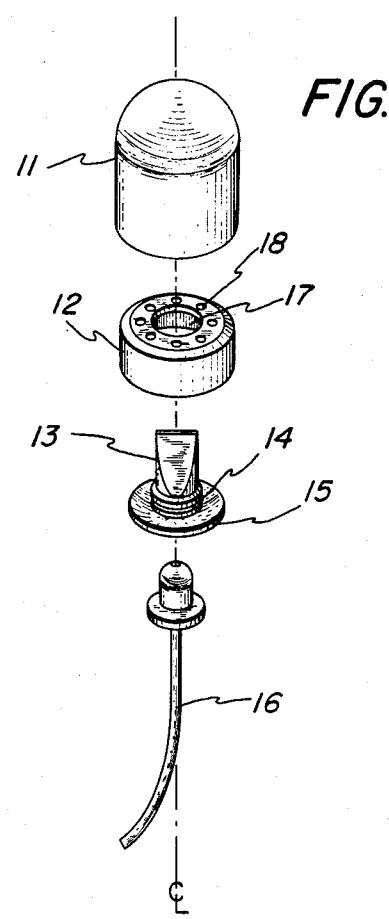
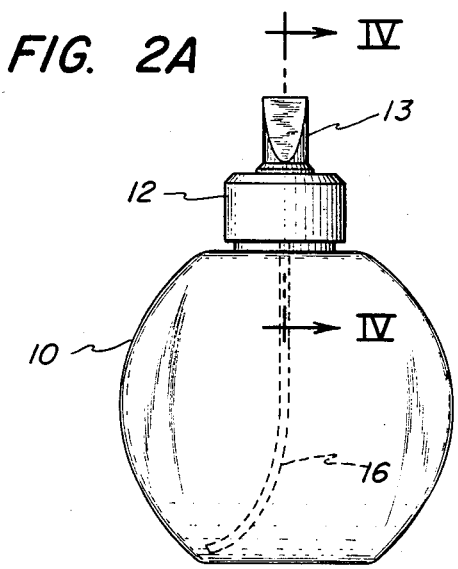
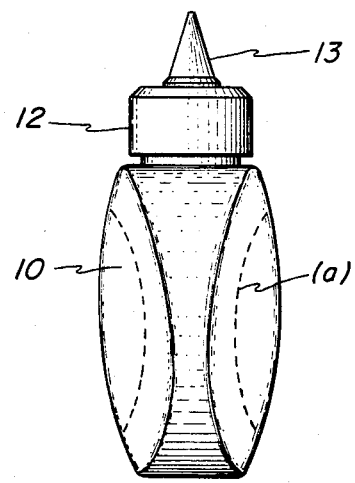

SPRAY DISPENSING CONTAINER AND VALVE THEREFOR

BACKGROUND

This invention relates to the field of spray dispensers of the squeeze bottle type. More particularly, it relates to an improved spray dispenser of the squeeze bottle type for use in dispensing nasal sprays, which is of simple construction and which provides means for preventing return of air throug the dispensing orifice.

Spray dispensers of the squeeze bottle type are widely used to administer to the nasal passages liquids containing an anti-cholinergic or decongestant for the relief of sinus congestion or acute or allergic rhinitis caused by conditions such as hay fever, allergies or the common cold. Such spray dispeners should be so designed as to meet certain use criteria, but these criteria are not entirely met by dispensers now in current commercial use.

Thus the dose regimen for each dispenser must be carefully controlled, because if a vasoconstrictor, normally present in nasal decongestant sprays, is over-administered, the resulting excessive vasoconstriction leads to rebound vasodilation of the blood vessels when the effect of the vasoconstrictor wears off. This in turn can produce an intensified congestion, called "rebound congestion", which can tend to perpetuate the rhinitis condition. This problem can be addressed, of course, by controlling the volume of the dosing mechanism, so as to thereby control the per dose medication, and by controlling the total volume of the dispensing container, within the limits allowed by the operating mechanism of the dispenser, so as to control the total available medication. A total dosing regimen for a single dispenser should ideally be sufficient for about seven days, the typical duration of the common cold.

Dispensers of this type should also be provided with a return air passage different from, and relatively remote from, the spray passage so as to prevent, or at least to minimize, inspiration of air through the exit passage during the recovery portion of a use cycle which would otherwise cause contamination of the dispenser contents.

In order to provide effective coverage of the mucous membranes, the dispenser should also be so designed that air and the liquid medication in the dispenser are well-mixed in the dispensing head in order that the material be dispensed as a fine spray rather than as a liquid steam or large droplets.

Finally, because of the shape of the nasal fossae, i.e. the cavities on either side of the midline of the face and lying directly behind the nares or nasal openings, the spray pattern delivered by the dispenser should advantageously be relatively oval, or elliptically, shaped, rather than circular as in conventional spray dispensers, in order to better insure reaching all surfaces of the fossae, which are generally triangular in cross sectional shape, tapering from about 15 mm. wide at the bottom to about 1 mm. wide at the top.

As will be seen, the dispensers provided by the present invention overcome these problems and meet the basic criteria for nasal spray dispensers, as described above, by use of a relatively simple dispensing head section, which consists of only three basic parts, in combination with a conventional squeeze bottle.

THE PRIOR ART

Efforts to overcome some of the problems discussed above in squeeze-type spray dispensers, especially those adapted for use as nasal spray dispensers, are described in the prior art, and particularly in the patent literature.

Thus U.S. Pat. No. 3,176,883 describes a squeeze-bottle type dispenser having a valve arrangement to prevent inspiration of air through the dispensing opening. The dispenser requires a valve 28 at the bottom of dip tube 17. Pressure on the bottle drives fluid up tube 17 to an exit port 15. Simultaneously air is forced through opening 53, through air discharge openings 26, through valves 25 and thence through grooves 20 to exit port 15. When pressure is released, valve 36 opens, while valves 25 and 30 close, and air passes from ports 44 and 35 back into the system. The sprayer disclosed thus would deliver a generally circular spray pattern and furthermore is relatively complicated and would be expensive to manufacture.

U.S. Pat. No. 3,519,208 describes a squeeze-type spray dispenser provided with means to prevent inspiration of air through the exit opening in which, upon squeezing the container, fluid is driven upward through dip tube 68 and out of orifice 72, while air is simultaneously forced through openings 66 in valve plate 30 and thence through passage 78 where it mixes with fluid exiting from the dip tube. On compression of the bottle, valve plate 30 is forced upward to thereby seal off air inlet openings 62, but when pressure on the bottle is released, the valve plate 30 drops away from openings 62 allowing the inward passage of air. The dispenser is designed primarily for uses other than as nasal spray dispensers, and as described would not be suitable for such use. In any event the dispensing mechanism requires complicated shapes which would be molded from plastic and would thus be expensive to manufacture.

U.S. Pat. No. 3,648,903 involves a concept generally similar to that described in U.S. Pat. No. 3,519,208 discussed above, except that the inlet openings are located on the surface of the dispenser head rather than at the base of an annular space as in U.S. Pat. No. 3,519,208. Like the dispenser described in the latter, the dispenser disclosed in U.S. Pat. No. 3,648,903 is not adapted for nasal spray use.

U.S. Pat. Nos. 3,794,247 and 4,093,124 involve concepts quite similar to that described in U.S. Pat. No. 3,519,208 discussed above. That is, air inlet openings to provide return of air to the interior of the dispenser after squeezing the same are provided at the base of an annular space surrounding the dispensing head. Like the dispenser of U.S. Pat. No. 3,519,208, the dispensers of U.S. Pat. Nos. 3,794,247 and 4,093,124 would require relatively complicated parts and are not adaptable to nasal spray dispensers.

U.S. Pat. No. 4,102,476 discloses an atomizer having provision for return of air to the dispensing container. However the air relief and exit paths are essentially lateral with the dispensing orifice, and thus the dispenser cannot be adapted for use as a nasal sprayer.

BRIEF SUMMARY OF THE INVENTION

The nasal spray dispensers of the present invention overcome the various disadvantages of the prior art dispensers discussed above, and furthermore the dispensers of this invention accomplish these results in a relatively simple manner.

More specifically the spray dispensers of the present invention are composed of only four separate parts in combination, namely a squeeze bottle; a closure cap therefor; a dip tube within the container; and a one piece combination dispensing nozzle which serves a threefold function as (1) a spray dispensing nozzle, (2) a check valve against inspiration of air through the nozzle and (3) a valve to permit inspiration of air into the container at a point removed from the exit nozzle.

BRIEF DESCRIPTION OF THE DRAWINGS

The invention is described below with reference to the accompanying drawings wherein:

FIG. 1 is a perspective view of a squeeze bottle dispenser with an attached overcap.

FIG. 2A is a side elevational view of the nasal spray dispenser of the invention, with the overcap removed, as the dispenser would appear when ready for use.

FIG. 2B is an end elevational view of the nasal spray dispenser of the invention, with the overcap removed, as the dispenser would appear when ready for use.

FIG. 3 is an exploded perspective view of the dispensing head portion of the nasal spray dispenser unit of the invention consisting of a dip tube, a combination dispensing nozzle and two-way check valve unit, a closure cap and an overcap.

DETAILED DESCRIPTION OF THE INVENTION

Figure 4A:
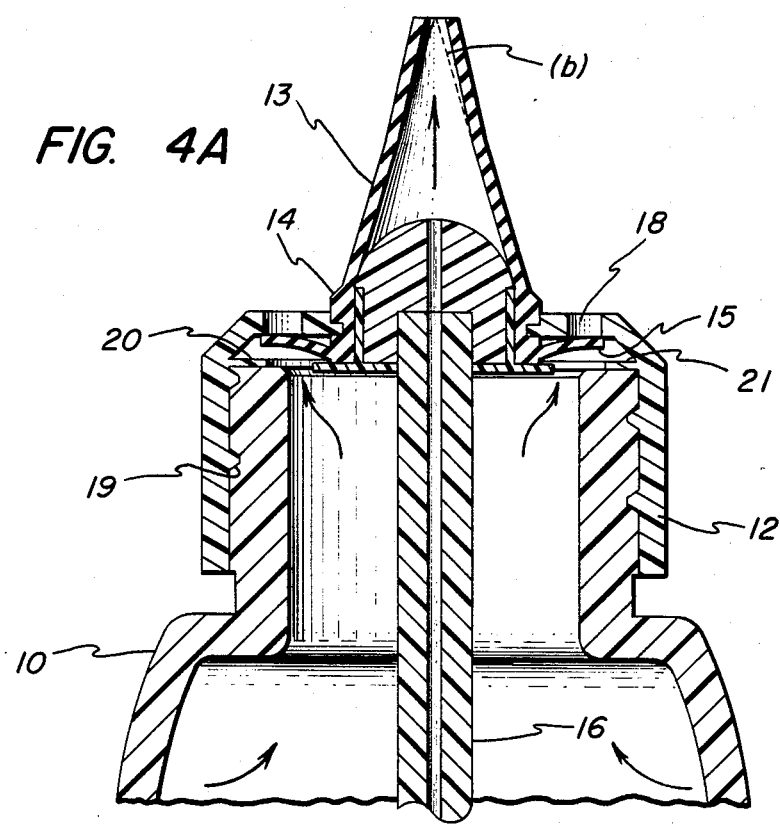
FIG. 4A is an enlarged cross sectional view on line IV—IV of FIG. 2A showing the parts of the dispensing head as they would appear during the dispensing part of a use cycle.

The invention will now be described in detail with reference to the foregoing drawings wherein like numerals are used to identify like parts.

FIG. 1 shows a conventional squeeze bottle used in the practice of the invention, generally indicated by reference numeral 10, which may optionally be fitted with an overcap 11 when not in use. The bottle is made of flexible material conventionally used in dispensers of the squeeze bottle type, which are inert to the contents of the bottle, including polyethylene, polypropylene, vinyl, flexible compositions of polystyrene, plasticized polyvinyl chloride or nylon.

As shown in FIGS. 2A and 2B, removal of the overcap exposes the dispensing head of the spray unit, which comprises a closure cap 12 to which is fitted a combination spray nozzle/two-way check valve unit 13.

The relationship between the various parts of the dispensing unit (less the bottle 10) is best seen with reference to FIG. 3. As there indicated, the dispensing head unit comprises several parts in combination, namely the overcap 11 previously described which is removably attached, for example by frictional engagement, to the closure cap 12. The latter, which is removably attached to the neck of bottle 10 by, for example, frictional engagement or by a screw threaded attachment 19 (see FIGS. 4A and 4B), is equipped with a series of air inlet or relief holes 18, whose purpose will be shortly described, and a central hole 17 for receiving a flexible spray nozzle unit 13, the latter being equipped with a retention shoulder 14 and a flexible flange 15. As will be seen, the integral construction of the spray nozzle unit 13 with the flexible flange 15 allows the unit to function as a two-way check valve. Finally the dispensing unit is equipped with a dip tube 16 which serves to conduct fluid from within the bottle 10 to the spray nozzle 13.

Figure 4B:
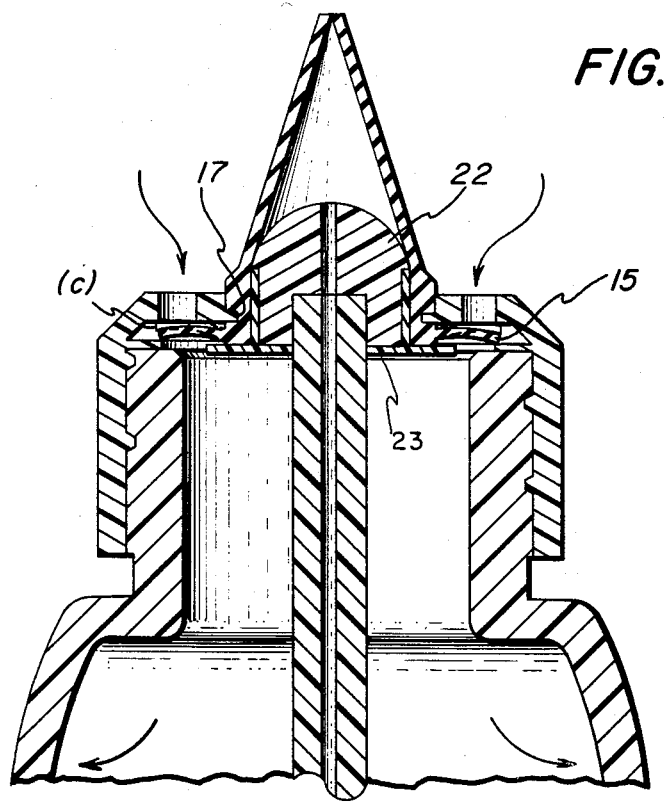
FIG. 4B is an enlarged cross sectional view on line IV—IV of FIG. 2A showing the parts of the dispensing head as they would appear during the recovery part of a use cycle.

The assembled spray unit is shown in FIGS. 4A and 4B where it will be seen that the spray nozzle/two-way check valve 13 is fitted to the closure cap 12 by inserting the neck of the spray nozzle through the central hole 17 of the cap. The nozzle unit is held in position in the cap by retention shoulder 14, which bears against the outer surface of the top wall of the cap, and by an annular rim 20 around the inside of the closure cap, which serves to capture and hold the flexible flange 15 within an annular cavity 21 defined by the rim 20, the inner face of the top wall of the cap and the upper portion of the side skirt of the cap. The dip tube 16 is fitted with a flanged head portion 22 which is inserted into the lower opening to the spray nozzle 13 and is maintained in such position by frictional engagement. A separate flanged collar member 23 is inserted between the flanged head portion 22 and the spray nozzle 13 to aid in or maintain the frictional engagement between the head portion 22 and the spray nozzle 13. The flanged collar member 23 also serves to support the dip tube 16 within the head portion 22.

As shown in FIG. 2A, the dip tube 16 extends to the bottom of squeeze bottle 10 which thus permits conveying the entire contents of the bottle to the dispensing head section, the contents of the bottle being forced upward to the spray nozzle by the inward flexing of the side walls of the bottle as indicated by the dotted lines (a) in FIG. 2B.

The operation of the dispensing unit will now be described with reference to FIGS. 4A and 4B. Referring first to FIG. 4A, when the bottle with the attached spray dispensing assembly is squeezed, air flow within the bottle, indicated by the arrows, forces the flexible flange 15 of the spray nozzle 13 upward from its normal position against the inside face of the top wall of the cap 12 where it closes off air inlet holes 18. With the air inlet holes thus sealed, continued inward pressure on the sides of the bottle forces liquid from the bottle upward through the dip tube and into the spray nozzle 13 from which it is ejected.

The spray nozzle is made of a highly resilient material, such as natural or synthetic elastomers or rubbers, for example vinyl or butyl rubbers, including brominated or chlorinated butyl rubbers. As seen in FIGS. 2A and 2B, the nozzle tip has a chisel like shape, and the exit nozzle comprises a transverse slit across the end of the tip between the opposing lips thereof. Thus in operation, as the liquid admixed with air is forcefully ejected from the nozzle tip, or a so-called duck bill valve, the latter, because of the resilience thereof, is caused to rapidly vibrate, in the fashion of a flutter valve, from an open to a closed position as shown by the dotted lines (b) in FIG. 4A. The air and liquid contents are forced up via dip tube 16 and through the orifice in the head of flanged head portion 22, and the latter causes the liquid to be broken up into fine droplets or a spray, the pattern of which will tend to conform to the shape of the open nozzle, i.e. generally elliptical.

As shown in FIG. 4B, when inward pressure on the side of the bottle is relaxed, the spray nozzle tip will close, thus preventing inspiration of air through the nozzle, but the flexible flange 15 of the spray nozzle, a so-called umbrella valve, will return to its normal position, thus opening air inlet holes 18 and permitting air, indicated by the arrows, to return to the bottle thereby completing a squeeze and recovery cycle. The dispenser is then ready for a dispensing portion of another cycle.

It will be understood that, although preferred embodiments have been described above in order to better illustrate the invention, alternative materials, forms and the like can be substituted for such aspects specifically described herein without either departing from the spirit of the invention or in any way adversely affecting the operability of the same.

For example, it will be appreciated that, although the spray dispensers of the present invention have been described with particular reference to nasal dispensers for use in dispensing the liquid contents as a spray, the dispensers can also be used for dispensing droplets by use of more gentle inward pressure on the bottle. When used as droplet dispensers, the dispensers of this invention would be inverted to fill the dip tube, and by application of gentle pressure, the contents dispensed drop by drop. Ideally only a "unit dose" held in the tube would be dispensed at a time, although continuous dropwise dispensing can be achieved by application of sufficient pressure to force liquid into the tube from the bottle. Use of the dispensers as droplet dispensers is thus also contemplated.

Having thus described the invention and the advantages thereof, it is considered that the invention is to be broadly construed and limited only by the character of the following claims.

We claim:

1. In a squeeze bottle dispenser for use in the administration of nasal sprays having means for preventing inspiration of air through the exit opening of said dispenser during the recovery portion of a use cycle in order to thereby prevent contamination of the dispenser contents, the improvement for attachment to, and use with, a said squeeze bottle which comprises in combination: a closure cap defined generally by a top wall and a side skirt for removable attachment to the neck of said squeeze bottle, said cap having (1) one or more air inlet holes and a central hole in said top wall and (2) means for retaining within said central hole; a one piece, resilient spray nozzle unit comprising an exit nozzle portion and a flexible flanged portion and a flexible flanged portion; and a dip tube for conveying the contents of said bottle to said spray nozzle unit, said retaining means comprising an annular rim around the inside of said side skirt of said closure cap and spaced from said top wall thereof, said spray nozzle unit being adapted to function as a two-way valve whereby, during the dispensing portion of a use cycle, said air inlet hole or holes are sealed by said flexible flange while said nozzle is open, and whereby, during the recovery portion of a use cycle, said air inlet hole or holes are opened and said nozzle is closed.

2. The dispenser combination according to claim 1 wherein said closure cap is removably attached to said bottle by a screw-threaded engagement.

3. The dispenser combination according to claim 2 which includes an overcap removably attached to said closure cap.

4. The dispenser combination according to claim 3 wherein said overcap is screw-threadedly engaged with said closure cap.

5. The dispenser combination according to claim 4 wherein said exit nozzle comprises a transverse slit in the tip thereof.

6. The dispenser combination according to claim 5 adapted for use as a unit dose dispenser for spray.

7. The dispenser combination according to claim 5 adapted for use as a unit dose dispenser for droplets.

8. The dispenser combination according to claim 3 wherein said overcap is frictionally engaged with said closure cap.

9. The dispenser combination according to claim 8 wherein said exit nozzle comprises a tranverse slit in the tip thereof.

10. The dispenser combination according to claim 9 adapted for use as a unit dose dispenser for spray.

11. The dispenser combination according to claim 9 adapted for use as a unit dose dispenser for droplets.

12. The dispenser combination according to claim 1 wherein said closure cap is removably attached to said bottle by a friction fit engagement.

13. The dispenser combination according to claim 12 which includes an overcap removably attached to said closure cap.

14. The dispenser combination according to claim 13 wherein said overcap is screw-threadedly engaged with said closure cap.

15. The dispenser combination according to claim 14 wherein said exit nozzle comprises a transverse slit in the tip thereof.

16. The dispenser combination according to claim 15 adapted for use as a unit dose dispenser for spray.

17. The dispenser combination according to claim 15 adapted for use as a unit dose dispenser for droplets.

18. The dispenser combination according to claim 13 wherein said overcap is frictionally engaged with said closure cap.

19. The dispenser combination according to claim 18 wherein said exit nozzle comprises a transverse slit in the tip thereof.

20. The dispenser combination according to claim 19 adapted for use as a unit dose dispenser for spray.

21. The dispenser combination according to claim 19 adapted for use as a unit dose dispenser for droplets.

* * * * *

UNITED STATES PATENT AND TRADEMARK OFFICE
CERTIFICATE OF CORRECTION

PATENT NO. : 4,513,891
DATED : April 30, 1985
INVENTOR(S) : Hain et al.

It is certified that error appears in the above-identified patent and that said Letters Patent are hereby corrected as shown below:

Column 1, line 11, change "throug" to read -- through --.

Column 1, line 51, change "steam" to read -- stream --.

Column 5, Claim 1, line 46, delete -- and a flexible flanged portion -- (first occurrence).

Signed and Sealed this

Fifteenth Day of October 1985

[SEAL]

Attest:

DONALD J. QUIGG

Attesting Officer

Commissioner of Patents and Trademarks—Designate